(12) United States Patent
Suyama et al.

(10) Patent No.: US 8,142,357 B2
(45) Date of Patent: Mar. 27, 2012

(54) CONDITION MONITORING DEVICE AND MONITOR MAIN UNIT FOR CONDITION MONITORING DEVICE

(75) Inventors: Mari Suyama, Aichi (JP); Toshinobu Mizutani, Aichi (JP); Masato Nishikawa, Aichi (JP)

(73) Assignee: Kabushiki Kaisha Tokai Rika Denki Seisakusho, Aichi (JP)

( * ) Notice: Subject to any disclaimer, the term of this patent is extended or adjusted under 35 U.S.C. 154(b) by 606 days.

(21) Appl. No.: 11/936,981

(22) Filed: Nov. 8, 2007

(65) Prior Publication Data
US 2008/0114217 A1 May 15, 2008

(30) Foreign Application Priority Data
Nov. 10, 2006 (JP) .................................. 2006-305460

(51) Int. Cl.
*A61B 5/00* (2006.01)
*G04B 47/00* (2006.01)
*G04B 47/06* (2006.01)
*A44C 5/00* (2006.01)
(52) U.S. Cl. ........... 600/301; 600/300; 368/11; 368/281
(58) Field of Classification Search .................. None
See application file for complete search history.

(56) References Cited

U.S. PATENT DOCUMENTS

| | | | |
|---|---|---|---|
| 6,396,416 B1 | 5/2002 | Kuusela et al. | |
| 6,452,162 B1 * | 9/2002 | Matsuno et al. | 250/239 |
| 6,619,835 B2 | 9/2003 | Kita | |
| 7,187,292 B2 | 3/2007 | Hayashi et al. | |
| 7,220,220 B2 * | 5/2007 | Stubbs et al. | 482/72 |
| 7,618,260 B2 * | 11/2009 | Daniel et al. | 439/37 |
| 2002/0188183 A1 | 12/2002 | Kusakabe et al. | |
| 2005/0171444 A1 | 8/2005 | Ono et al. | |

FOREIGN PATENT DOCUMENTS

| | | |
|---|---|---|
| CN | 1390109 A | 1/2003 |
| CN | 2792412 Y | 7/2006 |
| GB | 2 411 337 A | 8/2005 |
| JP | 2000-512414 | 9/2000 |
| JP | 2001-198110 | 7/2001 |
| JP | 2002-040175 | 2/2002 |
| JP | 2002-336281 | 11/2002 |
| JP | 2005-034520 | 2/2005 |
| JP | 2006-081838 | 3/2006 |
| WO | WO 01/01855 A1 | 1/2001 |
| WO | WO 2004/078033 A2 | 9/2004 |
| WO | WO 2006/076498 A2 | 7/2006 |

* cited by examiner

*Primary Examiner* — Henry M. Johnson, III
*Assistant Examiner* — Shirley Jian
(74) *Attorney, Agent, or Firm* — Patterson Thuente Christensen Pedersen, P.A.

(57) ABSTRACT

A condition monitoring device for monitoring conditions related to a user. A monitor main unit includes a connection structure for detachably attachment to a first sensor unit. The first sensor unit includes a first connector mated with the connection structure of the monitor main unit and a second connector detachably attachable to a second sensor unit. Data associated with the monitored condition detected by the first sensor unit is provided to the monitor main unit via the first connector and the connection structure. Data associated with a monitored condition detected by the second sensor unit is provided to the monitor main unit via the second connector, the first sensor unit, the first connector, and the connection structure.

9 Claims, 2 Drawing Sheets

Fig.2

CONDITION MONITORING DEVICE AND MONITOR MAIN UNIT FOR CONDITION MONITORING DEVICE

RELATED APPLICATION

The present application claims the benefit of priority to Japanese Patent Application No. 2006-305460 filed on Nov. 10, 2006. Said application is incorporated by reference herein.

BACKGROUND OF THE INVENTION

The present invention relates to a condition monitoring device and a monitor main unit for a condition monitoring device.

Japanese Laid-Open Patent Publication No. 2005-34520 describes a physical state monitoring system including a perspiration sensor arranged in a portable device carried by a driver. The portable device transmits data associated with the driver's perspiration amount, which is detected by the sensor. The data is received by an automobile. The automobile determines the physical state of the driver obtained from the data and shows the physical state on a display unit. A heart rate (pulse) sensor or a blood pressure sensor may be arranged in the portable device in lieu of or in addition to the perspiration sensor. In such a case, the driver's physical state is determined from the driver's heart rate (pulse) or blood pressure in lieu of or in addition to the driver's perspiration amount and shown on the display.

SUMMARY OF THE INVENTION

In the physical state monitoring system of the above publication, the portable device maker selects the sensors, which are integrally incorporated in the portable device.

Different users wish to incorporate different types of sensors in the portable device. Accordingly, the portable device must be versatile to satisfy the needs of many users. As a result, when only one type of the portable device is manufactured, the portable device must incorporate many types of sensors. Therefore, the portable device may incorporate a sensor that is useful for one user but not for another user. For a user purchasing a portable device, an undesirable sensor would raise the initial purchasing cost of the portable device. Further, such an undesirable sensor would add to the weight of the portable device and obstruct miniaturization of the portable device.

However, if the portable device maker were to satisfy the potential needs of each user, the maker would have to manufacture many types of the portable device. This increases the manufacturing types of portable devices, lowers production efficiency, and complicates inventory and shipment management.

The present invention provides a condition monitoring device and a monitor main unit for a condition monitoring device that are economic.

One aspect of the present invention is a monitor main unit for a condition monitoring device in which the condition monitoring device is carriable by a user and monitors a condition related to the user with a sensor unit. The monitor main unit includes a connection structure for detachable attachment of the sensor unit for detection of the monitored condition to the monitor main unit so that the monitor main unit acquires data associated with the monitored condition from the sensor unit.

A further aspect of the present invention is a condition monitoring device for monitoring conditions related to a user. The condition monitoring device includes a first sensor unit, carried by the user, for detecting a monitored condition. A monitor main unit includes a connection structure detachably attachable to the first sensor unit. The first sensor unit includes a first connector mateable with the connection structure of the monitor main unit and a second connector detachably attachable to a second sensor unit carriable by the user. Data associated with the monitored condition detected by the first sensor unit is provided to the monitor main unit via the first connector and the connection structure and processed by the monitor main unit. Data associated with a monitored condition detected by the second sensor unit is provided to the monitor main unit via the second connector, the first sensor unit, the first connector, and the connection structure and processed by the monitor main unit.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE PREFERRED EMBODIMENTS

A condition monitoring device according to a preferred embodiment of the present invention will now be described. In the preferred embodiment, conditions monitored by the condition monitoring device include the environmental state and physical state of a user.

Figure 1A:
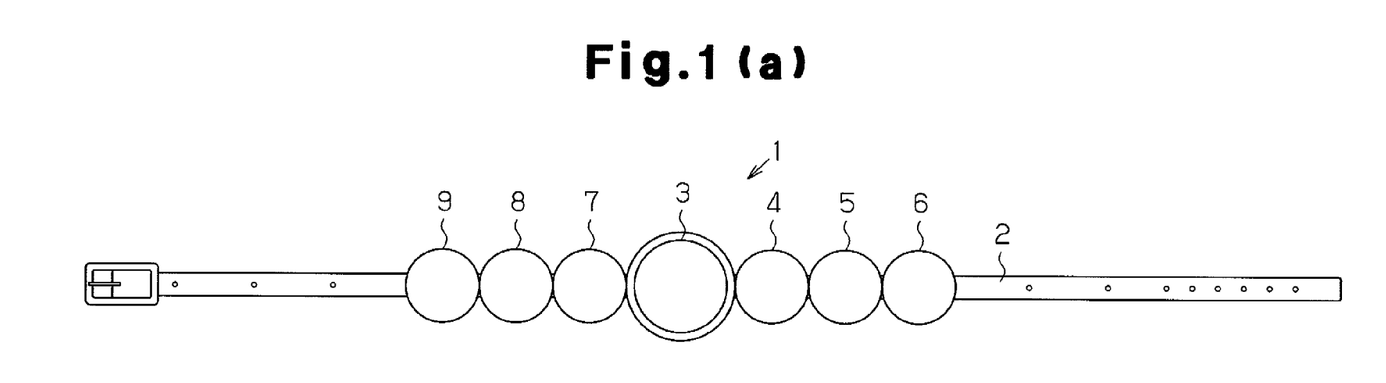
FIG. 1(a) is a plan view of a condition monitoring device according to a preferred embodiment of the present invention.
Figure 1B:
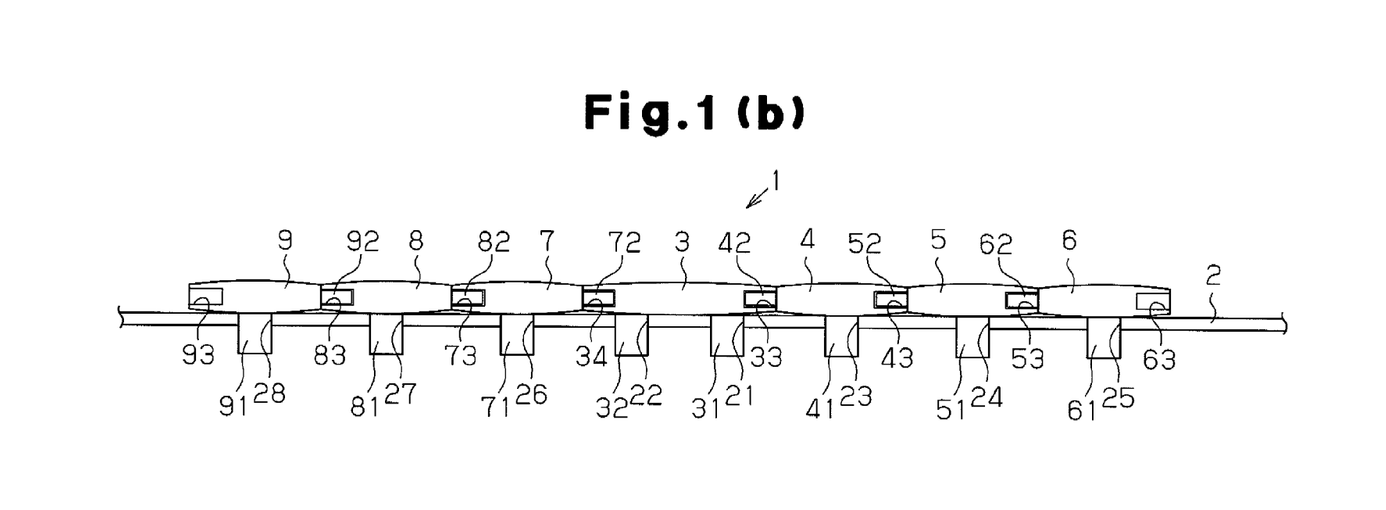
FIG. 1(b) is a partially enlarged cross-sectional view of the condition monitoring device of FIG. 1(a)

As shown in FIGS. 1(a) and 1(b), the condition monitoring device 1 includes a monitor main unit 3 attached to a band 2, which functions as a supporting member. An ambient temperature sensor unit 4, a humidity sensor unit 5, and an ultraviolet sensor unit 6 are connected in series along the band 2 in this order at one side of the monitor main unit 3. A body temperature sensor unit 7, a heart beat sensor unit 8, and a skin moisture sensor unit 9 are connected in series along the band 2 in this at the other side of the monitor main unit 3. The user puts on the condition monitoring device 1 by wearing the band 2 on his or her arm. The condition monitoring device 1 is also referred to as a portable remote condition monitoring device or a wearable condition monitoring device.

The ambient temperature sensor unit 4, the humidity sensor unit 5, the ultraviolet sensor unit 6, the body temperature sensor unit 7, the heart beat sensor unit 8, and the skin moisture sensor unit 9 are each smaller than the monitor main unit 3. In the preferred embodiment, the sensor units 4 to 9 are circular and have identical shapes and dimensions. Each sensor unit 4 to 9 has a thickness that is substantially the same as that of the monitor main unit 3. Each sensor unit 4 to 9 is one example of an external sensor unit.

The band 2 has flexibility and elastically deformable. Two attachment holes 21 and 22 extend through the longitudinally middle part of the band 2. The attachment hole 21 is formed slightly towards a distal end of the band 2 from a longitudinally central point of the band 2. The attachment hole 22 is formed slightly towards a basal end of the band 2 from the longitudinally central point of the band 2. Two pins 31 and 32 are formed at a central part of the rear surface of the monitor main unit 3. The monitor main unit 3 is detachably attached to the band 2 by fitting the pin 31 into the attachment hole 21 and fitting the pin 32 into the attachment hole 22.

The pins 31 and 32 each have a diameter that is slightly larger than that of the attachment holes 21 and 22. The pins 31 and 32 are press-fitted to the attachment holes 21 and 22 against the elastic force of the band 2. The pins 31 and 32 each have a length that is greater than the depth of the attachment holes 21 and 22, that is, the thickness of the band 2. The pins 31 and 32 each have a distal end face that comes into close contact with a user's arm when the band 2 is worn. The projecting length of the pins 31 and 32 from the rear surface of the band 2 is set so that the user does not feel pain at the arm when wearing the band 2. The distal end face of each of the pins 31 and 32 may be rounded so that the user does not feel pain at the arm.

The distal end face of each of the pins 31 and 32 defines a surface that contacts the user's arm. A reference potential electrode and a communication electrode are exposed from the distal end face of the pin 31 and the distal end face of the pin 32. The reference potential electrode and the communication electrode use the user's body as a signal transmission path so as to realize in-body communication between the condition monitoring device 1 and the automobile. The reference potential electrode, the communication electrode, and the in-body communication are not essential parts of the present embodiment and thus will not be described in detail.

A line of spaced attachment holes 23 to 25 are formed towards the distal end of the band 2 from the attachment hole 21. A line of spaced attachment holes 26 to 28 are formed towards the basal end of the band 2 from the attachment hole 22. The attachment holes 23 to 28 have the same diameter.

A pin 41 is formed at the middle part of the rear surface of the ambient temperature sensor unit 4. The ambient temperature sensor unit 4 is detachably attached to the band 2 by fitting the pin 41 into the attachment hole 23.

The pin 41 has a diameter that is slightly greater than that of the attachment hole 23. The pin 41 is press-fitted to the attachment hole 23 against the elastic force of the band 2. The pin 41 has a length that is greater than the depth of the attachment hole 23, that is, the thickness of the band 2. The pin 41 has a distal end face that comes into close contact with the user's arm of the user when the band 2 is worn. The projecting length of the pin 41 from the rear surface of the band 2 is set so that the user does not feel pain at the arm when the band 2 is worn. The distal end face of the pin 41 may be rounded so that the user does not feel pain at the arm.

In the ambient temperature sensor unit 4, an ambient temperature sensor is exposed from a front surface, which is opposite the rear surface of the pin 41. The temperature sensor detects the ambient temperature (also referred to as environmental temperature) at the location of the user. The ambient temperature is one parameter of the user's environmental state.

A pin 51 is formed at a middle part of the rear surface of the humidity sensor unit 5. The humidity sensor unit 5 is detachably attached to the band 2 by fitting the pin 51 into the attachment hole 24.

The pin 51 has a diameter that is slightly larger than that of the attachment hole 24. The pin 51 is press-fitted to the attachment hole 24 against the elastic force of the band 2. The pin 51 has a length that is greater than the depth of the attachment hole 24, that is, the thickness of the band 2. The pin 51 has a distal end face that comes into close contact with the user's arm when the band 2 is worn. The projecting length of the pin 51 from the rear surface of the band 2 is set so that the user does not feel pain at the arm when the band 2 is worn. The distal end face of the pin 51 may be rounded so that the user does not feel pain at the arm.

In the humidity sensor unit 5, a humidity sensor is exposed from a front surface, which is opposite the rear surface of the pin 51. The humidity sensor detects the humidity at the location of the user. The humidity is one parameter of the user's environmental state.

A pin 61 is formed at a middle part of the rear surface of the ultraviolet sensor unit 6. The ultraviolet sensor unit 6 is detachably attached to the band 2 by fitting the pin 61 into the attachment hole 25.

The pin 61 has a diameter that is slightly larger than that of the attachment hole 25. The pin 61 is press-fitted to the attachment hole 25 against the elastic force of the band 2. The pin 61 has a length that is greater than the depth of the attachment hole 25, that is, the thickness of the band 2. The pin 61 has a distal end face that comes into close contact with the user's arm when the band 2 is worn. The projecting length of the pin 61 from the rear surface of the band 2 is set so that the user does not feel pain at the arm when the band 2 is worn. The distal end face of the pin 61 may be rounded so that the user does not feel pain at the arm.

In the ultraviolet sensor unit 6, an ultraviolet sensor is exposed from a front surface, which is opposite the rear surface of the pin 61. The ultraviolet sensor detects the intensity or dose of ultraviolet light received by the user. The intensity or dose of ultraviolet light is one parameter of the user's environmental state.

A pin 71 is formed at the middle part of the rear surface of the body temperature sensor unit 7. The body temperature sensor unit 7 is detachably attached to the band 2 by fitting the pin 71 into the attachment hole 26.

The pin 71 has a diameter that is slightly greater than that of the attachment hole 26. The pin 71 is press-fitted to the attachment hole 26 against the elastic force of the band 2. The pin 71 has a length that is greater than the depth of the attachment hole 26, that is, the thickness of the band 2. The pin 71 has a distal end face that comes into close contact with the user's arm when the band 2 is worn. The projecting length of the pin 71 from the rear surface of the band 2 is set so that the user does not feel pain at the arm when the band 2 is worn. The distal end face of the pin 71 may be rounded so that the user does not feel pain at the arm.

The distal end face of the pin 71 defines a surface that contacts the user's arm. A body temperature sensor is exposed from the distal end face of the pin 71. The body temperature sensor detects the user's skin temperature. The skin temperature is one parameter of the user's physical state.

A pin 81 is formed at the middle part of the rear surface of the heart beat sensor unit 8. The heart beat sensor unit 8 is detachably attached to the band 2 by fitting the pin 81 into the attachment hole 27.

The pin 81 has a diameter that is slightly larger than that of the attachment hole 27. The pin 81 is press-fitted to the attachment hole 27 against the elastic force of the band 2. The pin 81 has a length that is greater than the depth of the attachment hole 27, that is, the thickness of the band 2. The pin 81 has a distal end face that comes into close contact with the user's arm when the band 2 is worn. The projecting length of the pin 81 from the rear surface of the band 2 is set so that the user does not feel pain at the arm when the band 2 is worn.

The distal end face of the pin 81 may be rounded so that the user does not feel pain at the arm.

The distal end face of the pin 81 defines a surface that contacts the user's arm. A heart beat sensor is exposed from the distal end face of the pin 81. The heart beat sensor detects the heart beat of the user. The heart beat is one parameter of the user's physical state.

A pin 91 is formed at the middle part of the rear surface of the skin moisture sensor unit 9. The skin moisture sensor unit 9 is detachably attached to the band 2 by fitting the pin 91 into the attachment hole 28.

The pin 91 has a diameter that is slightly larger than that of the attachment hole 28. The pin 91 is press-fitted to the attachment hole 28 against the elastic force of the band 2. The pin 91 has a length that is greater than the depth of the attachment hole 28, that is, the thickness of the band 2. The pin 91 has a distal end face that comes into close contact with the user's arm when the band 2 is worn. The projecting length of the pin 91 from the rear surface of the band 2 is set so that the user does not feel pain at the arm when the band 2 is worn. The distal end face of the pin 91 may be rounded so that the user does not feel pain at the arm.

The distal end face of the pin 91 defines a surface that contacts the user's arm. A skin moisture sensor is exposed from the distal end face of the pin 91. The skin moisture sensor detects the user's skin moisture content. The skin moisture content is one parameter of the user's physical state.

A first connection structure is formed in the side of the monitor main unit 3. The first connection structure can be formed by a recess such as a female connector 33. A second connection structure is formed opposite to the female connector 33 in the side of the monitor main unit 3. The second connection structure can be formed by a recess such as a female connector 34.

A first connector that mates with the female connector 33 (first connection structure) is formed in the side of the ambient temperature sensor unit 4, which serves as a first sensor unit. The first connector can be formed by a projection such as a male connector 42. The ambient temperature sensor unit 4 is detachably attached to the monitor main unit 3 by fitting the male connector 42 to the female connector 33. A second connector is formed opposite to the male connector 42 in the side of the ambient temperature sensor unit 4. The second connector can be formed by a recess such as a female connector 43.

A third connector that mates with the female connector 43 (second connector) is formed in the side of the humidity sensor unit 5, which serves as a second sensor unit. The third connector can be formed by a projection such as a male connector 52. The humidity sensor unit 5 is detachably attached to the ambient temperature sensor unit 4 by fitting the male connector 52 to the female connector 43. A fourth connector is formed opposite to the male connector 52 in the side of the humidity sensor unit 5. The fourth connector can be formed by a recess such as a female connector 53.

A male connector 62 that mates with the female connector 53 (fourth connector) is formed in the side of the ultraviolet sensor unit 6, which serves as a third sensor unit. The ultraviolet sensor unit 6 is detachably attached to the humidity sensor unit 5 by fitting the male connector 62 to the female connector 53. A female connector 63 is formed opposite to the male connector 62 in the side of the ultraviolet sensor unit 6. The female connector 63 does not receive any male connector in the present embodiment.

A fifth connector that mates with the female connector 34 (second connection structure) is formed in the side of the body temperature sensor unit 7, which serves as a fourth sensor unit. The fifth connector can be formed by a projection such as a male connector 72. The body temperature sensor unit 7 is detachably attached to the monitor main unit 3 by fitting the male connector 72 to the female connector 34. A sixth connector is formed opposite to the male connector 72 in the side of the body temperature sensor unit 7. The sixth connector can be formed by a recess such as a female connector 73.

A seventh connector that mates with the female connector 73 (sixth connector) is formed in the side of the heart beat sensor unit 8, which serves as a fifth sensor unit. The seventh connector can be formed by a projection such as a male connector 82. The heart beat sensor unit 8 is detachably attached to the body temperature sensor unit 7 by fitting the male connector 82 to the female connector 73. An eighth connector is formed opposite to the male connector 82 in the side of the heart beat sensor unit 8. The eighth connector can be formed by a recess such as a female connector 83.

A male connector 92 that mates with the female connector 83 (eighth connector) is formed in the side of the skin moisture sensor unit 9, which serves as a sixth sensor unit. The skin moisture sensor unit 9 is detachably attached to the heart beat sensor unit 8 by fitting the male connector 92 to the female connector 83. A female connector 93 is formed opposite to the male connector 92 in the side of the skin moisture sensor unit 9. The female connector 93 does not receive any male connector in the present embodiment.

The female connectors 33, 34, 43, 53, 63, 73, 83, and 93 have the same structure. The male connectors 42, 52, 62, 72, 82, and 92 have the same structure. Therefore, in the present embodiment, except for its own sensor unit female connector, the male connectors 42, 52, 62, 72, 82, and 92 can each be mated with any one of the female connectors 33, 34, 43, 53, 63, 73, 83, and 93.

The female connectors 33, 34, 43, 53, 63, 73, 83, and 93 and male connectors 42, 52, 62, 72, 82, and 92 each have a contact or a terminal (not shown). When one female connector is fitted with one male connector, the contact or the terminal of the female connector is electrically connected to the contact or the terminal of the male connector. The sensor units 4 to 9 thus have connection compatibility.

Figure 2:
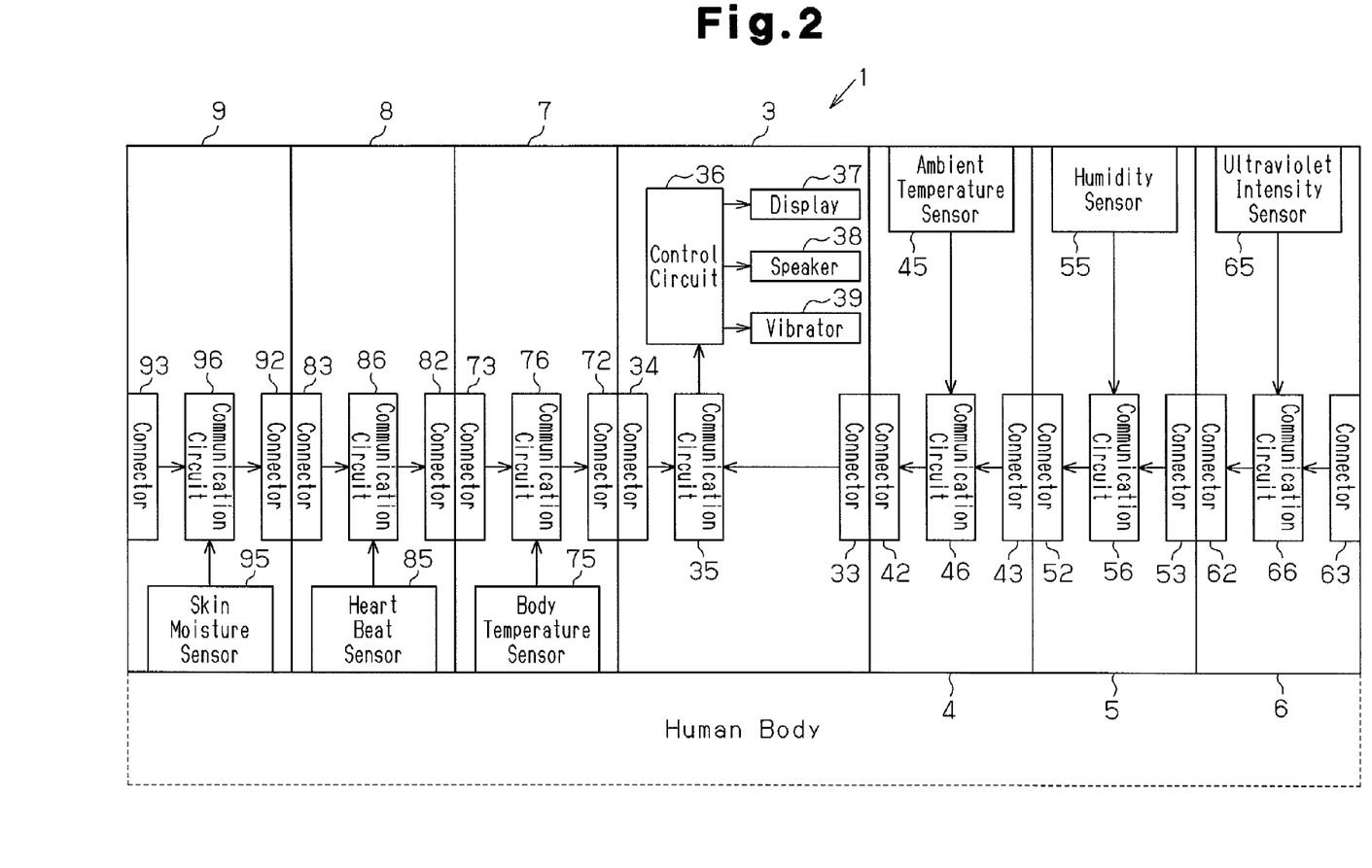
FIG. 2 is a block diagram of the condition monitoring device of FIG. 1(a).

The electrical configuration of the condition monitoring device 1 will now be described.

As shown in FIG. 2, the ambient temperature sensor unit 4 is electrically connected to the monitor main unit 3 of the condition monitoring device 1 by the female connector 33 and the male connector 42. The humidity sensor unit 5 is electrically connected to the ambient temperature sensor unit 4 by the female connector 43 and the male connector 52, and the ultraviolet sensor unit 6 is electrically connected to the humidity sensor unit 5 by the female connector 53 and the male connector 62.

The body temperature sensor unit 7 is electrically connected to the monitor main unit 3 of the condition monitoring device 1 by the female connector 34 and the male connector 72. The heart beat sensor unit 8 is electrically connected to the body temperature sensor unit 7 by the female connector 73 and the male connector 82, and the skin moisture sensor unit 9 is electrically connected to the heart beat sensor unit 8 by the female connector 83 and the male connector 92.

The ultraviolet sensor unit 6 detects the intensity or dose of ultraviolet light with an ultraviolet intensity or dose sensor 65 exposed from its front surface, converts the data representing the ultraviolet intensity or dose with a communication circuit 66 into a format easily handled by the monitor main unit 3, and provides the converted data to an adjacent external device (in this case, the humidity sensor unit 5) through the male connector 62. The ultraviolet sensor unit 6 provides the data acquired from a preceding external device (in this case, there is no external device connected to the female connector 63) via the female connector 63 to the following external device (in this case, humidity sensor unit 5) via the communication circuit 66 and the male connector 62.

The humidity sensor unit 5 detects the humidity with a humidity sensor 55 exposed from its front surface, converts the data representing the ambient humidity with a communication circuit 56 into a format easily handled by the monitor main unit 3, and provides the converted data to the adjacent external device (in this case, ambient temperature sensor unit 4) via the male connector 52. The humidity sensor unit 5 provides the data acquired from the preceding external device (in this case, ultraviolet sensor unit 6) via the female connector 53 to the following external device (in this case, ambient temperature sensor unit 4) via the communication circuit 56 and the male connector 52.

The ambient temperature sensor unit 4 detects the ambient temperature with a temperature sensor 45 exposed from its front surface, converts the data representing the ambient temperature with a communication circuit 46 into a format easily handled by the monitor main unit 3, and provides the converted data to the adjacent external device (in this case, monitor main unit 3) via the male connector 42. The ambient temperature sensor unit 4 provides the data acquired from the preceding external device (in this case, humidity sensor unit 5) via the female connector 43 to the following external device (in this case, monitor main unit 3) via the communication circuit 46 and the male connector 42.

In the skin moisture sensor unit 9, a skin moisture sensor 95 detects the user's skin moisture content. A communication circuit 96 converts the data representing the user's skin moisture content to a format easily handled by the monitor main unit 3. Then, the communication circuit 96 provides the converted data to the adjacent external device (in this case, heart beat sensor unit 8) via the male connector 92. When there is a preceding external device connected to the skin moisture sensor unit 9 by the female connector 93 (in the preferred embodiment, there is no external device connected by the female connector 93), the skin moisture sensor unit 9 provides the data acquired from the preceding external device to the following external device (in this case, heart beat sensor unit 8) via the communication circuit 96 and the male connector 92.

In the heart beat sensor unit 8, a heart beat sensor 85 detects the user's heart beat (or heart rate). A communication circuit 86 converts the data representing the user's heart beat (or heart rate) into a format easily handled by the monitor main unit 3. Then, the communication circuit 86 provides the converted data to the adjacent external device (in this case, body temperature sensor unit 7) via the male connector 82. The heart beat sensor unit 8 provides the data acquired from the preceding external device (in this case, skin moisture sensor unit 9) via the male connector 83 to the following external device (in this case, body temperature sensor unit 7) via the communication circuit 86 and the male connector 82.

In the body temperature sensor unit 7, a body temperature sensor 75 detects the user's skin temperature. A communication circuit 76 converts the data representing the user's skin temperature into a format easily handled by the monitor main unit 3. Then, the communication circuit 76 provides the converted data to the adjacent external device (in this case, monitor main unit 3) via the male connector 72. The body temperature sensor unit 7 provides the data acquired from the preceding external device (in this case, heart beat sensor unit 8) via the female connector 73 to the following external device (in this case, monitor main unit 3) via the communication circuit 76 and the male connector 72.

The monitor main unit 3 includes a communication circuit 35 that specifies the sensor units associated with the data acquired from the adjacent external device via the female connector 33 (in this case, the ambient temperature sensor unit 4). The communication circuit 35 further specifies the sensor units associated with the data acquired from the adjacent external device via the female connector 34 (in this case, the body temperature sensor unit 7). The communication circuit 35 of the monitor main unit 3 generates data in which the specification result and the level of data are associated and provides the data to a control circuit 36. The data is analyzed in the control circuit 36. The control circuit 36 of the monitor main unit 3 activates at least one of a display 37, a speaker 38, and a vibrator 39 in accordance with the conditions recognized from the analysis.

If the detected values of the ambient temperature, humidity, user's skin temperature, and the like are in a normal range, the control circuit 36 determines that the user's environmental state and physical state (monitored conditions) are at a "normal level". In this case, the control circuit 36 notifies the user of the "normal level" with the display 37, the speaker 38, and the vibrator 39. In the preferred embodiment, the display 37 displays a blue image such as blue mark or blue character or displays a background having blue as the basic tone, and the speaker 38 and the vibrator 39 are not activated, so that "normal level" is notified to the user.

If one or more of the detected values deviates from the normal range, for example, if the ambient temperature is higher than a reference temperature and the user's skin moisture content is less than the reference skin moisture content, the control circuit 36 determined that the monitored conditions is at a "caution level". In this case, the control circuit 36 notifies the user of the "caution level" with the display 37, the speaker 38, and the vibrator 39. In the preferred embodiment, the display 37 shows a yellow image, such as a yellow mark or a yellow character, or a background in a yellow tone. The vibrator 39 may also be activated.

If one or more detected values greatly deviates from the normal range or if the detected values indicate that the user's physical state may be seriously impaired, for example, if the intensity or dose of ultraviolet light greatly exceeds a reference value during the summertime, the control circuit 36 determines that the conditions of the monitored target is in a "danger level". In this case, the control circuit 36 notifies the user of the "danger level" using the display 37, the speaker 38, and the vibrator 39. In the preferred embodiment, the display 37 displays a red image, such as red mark or red character, or a background in a red tone. Further, the speaker 38 issues a warning.

The preferred embodiment has the advantages described below.

(1) The female connectors 33 and 34 for directly attaching the sensor unit to the monitor main unit 3 are arranged on the monitor main unit 3 of the condition monitoring device 1. Thus, from the plural types of sensor units having a male connector mated with the female connector 33 and 34, the user selects the sensor unit associated with the condition the user wishes to monitor. Then, the user attaches the selected sensor unit to the monitor main unit 3 with the female connector 33 or 34 so that the monitor main unit 3 acquires the data representing the state detected by the sensor unit. Therefore, the user can select the necessary sensor unit and connect the selected sensor unit to the monitor main unit 3. This is economical.

(2) The monitor main unit 3 includes a plurality of female connectors (in the preferred embodiment, a total of two female connectors 33 and 34) for directly attaching sensor units to the monitor main unit 3. Thus, by attaching the desired sensor units to the monitor main unit 3 with each of the plurality of female connectors, the monitor main unit 3 acquires data associated with various states in accordance with the number of sensor units. The sensor units are all selected by the user. This enables the condition monitoring device 1 to be tailor-made in accordance with the users intended purpose. Thus, the condition monitoring device 1 is economical.

(3) A plurality of female connectors (in the preferred embodiment, a total of two female connectors 33 and 34) having the same structure are arranged in the monitor main unit 3 so that sensor units can be directly attached to the monitor main unit 3. Thus, a sensor unit can be attached to the monitor main unit 3 by any of the female connectors. Therefore, the desired sensor unit is just required to be attached at the preferred position. This enables a creative condition monitoring device 1 to be tailor-made.

(4) The ambient temperature sensor unit 4 includes the male connector 42, which mates with the female connector 33 of the monitor main unit 3, and the female connector 43, which directly attaches the humidity sensor unit 5 to the ambient temperature sensor unit 4. The ambient temperature sensor unit 4 is attached to the monitor main unit 3, and the humidity sensor unit 5 is attached to the ambient temperature sensor unit 4. Thus, the monitor main unit 3 acquires the data associated with the condition detected by the ambient temperature sensor unit 4 as well as the data associated with the condition detected by the humidity sensor unit 5. The sensors units 4 and 5 are both selected by the user. This enables the condition monitoring device 1 to be tailor-made in accordance with the users intended purpose. Thus, the condition monitoring device 1 is economical.

(5) The body temperature sensor unit 7 includes the male connector 72, which mates with the female connector 34 of the monitor main unit 3, and the female connector 73, which directly attaches the heart beat sensor 8 to the body temperature sensor unit 7. The body temperature sensor unit 7 is attached to the monitor main unit 3, and the heart beat sensor unit 8 is attached to the body temperature sensor unit 7. Thus, the monitor main unit 3 acquires the data associated with the condition detected by the body temperature sensor unit 7 as well as the data associated with the condition detected by the heart beat sensor unit 8. The sensors units 7 and 8 are both selected by the user. This enables the condition monitoring device 1 to be tailor-made in accordance with the users intended purpose. Thus, the condition monitoring device 1 is economical.

(6) The ambient temperature sensor unit 4 is attached to the monitor main unit 3 by the female connector 33, the humidity sensor unit 5 is attached to the ambient temperature sensor unit 4, the body temperature sensor unit 7 is attached to the monitor main unit 3 by the female connector 34, and the heart beat sensor unit 8 is attached to the body temperature sensor unit 7. In this case, the monitor main unit 3 acquires the data associated with the conditions detected by the ambient temperature sensor unit 4 and the humidity sensor unit 5, as well as, the data associated with the conditions detected by the body temperature sensor unit 7 and the heart beat sensor unit 8. The sensors units 4, 5, 7, and 8 are selected by the user. This enables the condition monitoring device 1 to be tailor-made in accordance with the users intended purpose. Thus, the condition monitoring device 1 is economical.

(7) The monitor main unit 3 acquires data associated with the conditions detected by each of the ambient temperature sensor unit 4, the humidity sensor unit 5, the ultraviolet sensor unit 6, the body temperature sensor unit 7, the heart beat sensor unit 8, and the skin moisture sensor unit 9. The sensors units 4 to 9 are selected by the user. This enables the condition monitoring device 1 to be tailor-made in accordance with the users intended purpose. Thus, the condition monitoring device 1 is economical.

(8) The humidity sensor unit 5 includes the male connector 52, which mates with the female connector 43 of the ambient temperature sensor unit 4, and the female connector 53, which directly attaches the ultraviolet sensor unit 6 to the humidity sensor unit 5. The male connector 52 can also be mated with the female connector 33 of the monitor main unit 3, and the female connector 53 can also be mated with the male connector 42 of the ambient temperature sensor unit 4. Thus, the monitor main unit 3, the ambient temperature sensor unit 4, the humidity sensor unit 5 may be successively attached in this order. Alternatively, the order of the ambient temperature sensor unit 4 and the humidity sensor unit 5 may be changed so that they are attached in the order of the monitor main unit 3, the humidity sensor unit 5, and the ambient temperature sensor unit 4. Therefore, the desired sensor units may be attached in the preferred order. This enables a creative condition monitoring device 1 to be tailor-made.

(9) The heart beat sensor unit 8 includes the male connector 82, which mates with the female connector 73 of the body temperature sensor unit 7, and the female connector 83, which directly attaches the skin moisture sensor unit 9 to the heart beat sensor unit 8. The male connector 82 can also be mated with the female connector 34 of the monitor main unit 3, and the female connector 83 can also be mated with the male connector 72 of the body temperature sensor unit 7. Thus, the monitor main unit 3, the body temperature sensor unit 7, and the heart beat sensor unit 8 may be successively attached in this order. Alternatively, the order of the body temperature sensor unit 7 and the heart beat sensor unit 8 may be changed so that they are attached in the order of the monitor main unit 3, the heart beat sensor unit 8, and the body temperature sensor unit 7. Therefore, the desired sensor units may be attached in the preferred order. This enables a creative condition monitoring device 1 to be tailor-made.

(10) The male connector 42 of the ambient temperature sensor unit 4 mates with the female connector 33 of the monitor main unit 3. The male connector 72 of the body temperature sensor unit 7 can also be mated with the female connector 33 of the monitor main unit 3. The male connector 72 of the body temperature sensor unit 7 mates with the female connector 34 of the monitor main unit 3. The male connector 42 of the ambient temperature sensor unit 4 may also be mated with the female connector 34 of the monitor main unit 3. Thus, the ambient temperature sensor unit 4 may be attached to the monitor main unit 3 by the female connector 33, and the body temperature sensor unit 7 may be attached to the monitor main unit 3 by the female connector 34. Alternatively, the ambient temperature sensor unit 4 may be attached to the monitor main unit 3 by the female connector 34, and the body temperature sensor unit 7 may be attached to the monitor main unit 3 by the female connector 33. Therefore, the desired sensor units may be attached at the preferred positions. This enables a creative condition monitoring device 1 to be tailor-made.

(11) Except for its own sensor unit female connector, the male connectors 42, 52, 62, 72, 82, and 92 mates with any of the female connectors 33, 34, 43, 53, 63, 73, 83, and 93. Thus, for example, using the monitor main unit 3 as the starting point, the ambient temperature sensor unit 4, the humidity sensor unit 5, the ultraviolet sensor unit 6, the body temperature sensor unit 7, the heart beat sensor unit 8, and the skin moisture sensor unit 9 may be connected in series in this order (in this case, skin moisture sensor unit 9 is the terminating point). Therefore, the user selects the desired sensor units (in any quantity), and attaches the selected sensor units in the desired order and desired position. Thus, the condition monitoring device 1 can be tailor-made in accordance with the user's preference.

(12) In the illustrated embodiment, the monitor main unit 3 does not have any built-in sensors for detecting a condition related to the user. The sensor units are not incorporated and integrated in the monitor main unit 3 in advance. This enables reduction in the size and weight of the monitor main unit 3 and provides a wearable monitor main unit 3.

(13) The maker of the monitor main unit 3 is required to manufacture only one type of the monitor main unit 3. The sensor units attached afterwards depends on the preference of the user. This improves the productivity of the monitor main unit 3.

(14) The user of the condition monitoring device 1 purchases the monitor main unit 3 and the desired sensor units. Then, the user connects the purchased monitor main unit 3 and the sensor units. Thus, the condition monitoring device 1 suiting the needs of the user is tailor-made. This lowers the initial purchasing cost of the condition monitoring device 1 and is thus economical.

(15) The user can tailor the condition monitoring device 1 in accordance with his or her mood as if the user is wearing an accessory.

(16) The body temperature sensor 75, the heart beat sensor 85, and the skin moisture sensor 95 are each exposed to contact the user's arm. This improves detection accuracy and ensures detection of a physical amount (e.g., skin temperature) associated with the physical state of the user.

(17) Any sensor unit can be freely attached to the monitor main unit 3. Thus, a new sensor unit can be freely added, a sensor unit that has become unnecessary can be freely detached, and a defective sensor unit can be freely replaced with a new one. That is, addition, detachment, and replacement of sensor units are easily performed since any sensor unit may be selected and attached to the monitor main unit 3.

(18) The sensor units may be connected to the monitor main unit 3 just by inserting the male connector of a selected sensor unit into the female connector of either the monitor main unit 3 or another selected sensor unit, while press-fitting the pin on the rear surface of each sensor unit into a hole of the band 2. This procedure is reversed to detach the sensor units. Therefore, the attachment and detachment of the sensor units is simple and convenient.

(19) The pins are fitted into the band 2, while the male connectors are mated with the female connectors. This ensures connection and fastening of the monitor main unit 3 with a sensor unit or a sensor unit with another sensor unit. Therefore, after being connected with one another, the monitor main unit 3 and the sensor units are prevented from being separated.

It should be apparent to those skilled in the art that the present invention may be embodied in many other specific forms without departing from the spirit or scope of the invention. Particularly, it should be understood that the present invention may be embodied in the following forms.

The relationship of the female connector and the male connector may be reversed from the relationship in the preferred embodiment. That is, the female connectors 33 and 34 of the monitor main unit 3 may be changed to male connectors. The male connectors 42, 52, 62, 72, 82, and 92 of the sensor units 4 to 9 may be changed to female connectors. The female connectors 43, 53, 63, and 73 of the sensor units 4 to 9 may be changed to male connectors.

The female connector 33 and the female connector 34 of the monitor main unit 3 may have different structures.

The monitor main unit 3 may have one or three or more connection structures (female connector 33 and female connector 34). For example, if the monitor main unit 3 has four connection structures and the connection structures are arranged at equal intervals along the outer surface of the monitor main unit 3, the condition monitoring device 1 may be deployed so that the monitor main unit 3 and the sensor units are arranged in a cross-like manner Sensor units such as an atmospheric pressure sensor unit for detecting atmospheric pressure at the location of the user, an oxygen concentration sensor unit for detecting oxygen concentration at the location of the user, a blood pressure unit for detecting the user's blood pressure, a wrinkle advancement sensor unit for detecting the advancement of the user's wrinkles (or future advancement of wrinkles), a skin fineness sensor unit for detecting fineness of the user's skin, and a skin elasticity sensor unit for detecting elasticity of the user's skin may be used.

The condition monitoring device 1 is not limited to a wrist watch type device or bracelet type device worn on the user's arm, and may be a necklace type device or pendant type device worn around the neck of the user. Alternatively, the condition monitoring device 1 may be an eyeglass type device or a ring type device. If the conditions monitored by the condition monitoring device 1 is used as the user's physical information, it is preferred that the condition monitoring device 1 be shaped to come into close contact with the user. If the user of the condition monitoring device 1 is the driver of a vehicle, it is preferred that, for example, the monitor main unit 3 be integrated with a wrist watch, which is normally worn by the user regardless of whether or not the user rides the vehicle. In this case, the sensor units desired by the user are attachable to the wrist watch.

The supporting member is not limited to the band 2, and other supporting members, such as belt, a chain, a ring, eyeglasses, a safety pin, and the like may be used.

The monitor main unit 3 of the preferred embodiment may be used with an electronic key for a so-called keyless system that enables the locking and unlocking of a door for a vehicle, such as an automobile, or a building, such as a house, with a door lock controller when an unlock button or lock button of the electronic key is operated. In such a case, the monitor main unit 3 incorporates functions (keyless functions) necessary for the electronic key. For example, the monitor main unit 3 includes a function for transmitting an ID code signal including an unlock request code (lock request code) for requesting unlocking (locking) of the door and a unique ID code for the monitor main unit 3 (electronic key) when an unlock button (or a lock button) is operated. When such an ID code signal is received by the door lock controller, the ID code is verified with a reference ID code, and the unlocking (locking) of the door is enabled when the ID codes match.

Alternatively, the monitor main unit 3 of the preferred embodiment may be used with an electronic key for a so-called smart system that enables the locking and unlocking of a door for a vehicle, such as an automobile, or a building, such as a house, with a door lock controller when the proper key is located near the door. In such a case, the monitor main unit 3 incorporates functions (keyless functions) necessary for the electronic key. For example, the monitor main unit 3 includes a function for transmitting an ID code signal including a unique ID code for the monitor main unit 3 (electronic key) in response to a request signal cyclically transmitted from a door lock controller that monitors the approach of the monitor main unit 3 to the door. When such an ID code signal is received by the door lock controller, the ID code is verified with a reference ID code, and the unlocking (locking) of the door is enabled when the ID codes match.

If the smart function is incorporated in the monitor main unit 3, in addition to the locking and unlocking of a door, the starting of the vehicle engine may also be enabled.

If the monitor main unit 3 incorporates either one or both of the keyless function and the smart function, a user such as the driver of a vehicle or the resident of a building does not need to carry both of the electronic key and the condition monitoring device 1. This would improve the portability. If a vehicle and a building both have the keyless function and the smart function, the user does not need to hold three devices, which are the vehicle key, the building key, and the condition monitoring device 1. This would further improve the portability.

If the keyless function is incorporated in the monitor main unit 3, the information related to the user's environmental state or physical state is transmitted to a base control device when transmitting the ID code signal from the monitor main unit 3 to the base control device, which is arranged in the vehicle or the building. Such information may be used in the base control device.

If the smart function is incorporated in the monitor main unit 3, the information related to the user's environmental state or physical state is transmitted to a base control device when transmitting the ID code signal from the monitor main unit 3 to the base control device, which is arranged in the vehicle or the building. Such information can be used in the base control device. On the other hand, if the base control device transmits the information on the vehicle or the building to the monitor main unit 3 when transmitting the request signal from the base control device to the monitor main unit 3, such information may be used in the monitor main unit 3. For instance, when changing the setting of the base control device, the user may be notified of the change and requested for a so-called answer back.

The present examples and embodiments are to be considered as illustrative and not restrictive, and the invention is not to be limited to the details given herein, but may be modified within the scope and equivalence of the appended claims.

What is claimed is:

1. A condition monitoring device for monitoring conditions related to a user, the condition monitoring device comprising:
    a first sensor unit, carried by the user, configured to detect a monitored condition;
    a monitor main unit including a connection structure detachably attachable to the first sensor unit, the first sensor unit including a first connector mateable with the connection structure of the monitor main unit and a second connector detachably attachable to a second sensor unit carriable by the user, wherein; data associated with the monitored condition detected by the first sensor unit is provided to the monitor main unit via the first connector and the connection structure and processed by the monitor main unit; and data associated with a monitored condition detected by the second sensor unit is provided to the monitor main unit via the second connector, the first sensor unit, the first connector, and the connection structure and processed by the monitor main unit; and
    a supporting member configured to support the monitor main unit and a plurality of sensor units including the first and second sensor units to put the monitor main unit and the plurality of the sensor units on the user, the supporting member having attachment through holes, wherein the sensor units and the monitor main unit each have a pin configured to be press-fitted to one of the attachment through holes of the supporting member, each pin having a distal end face configured to come into close contact with the user when the user wears the supporting member supporting the sensor units and the monitor main unit, and wherein the pins of the first sensor unit and the monitor main unit are separated from one another by a fixed distance that corresponds to a distance between adjacent two attachment through holes of the supporting member in a state in which the first connector that is integrally formed on a side surface of the first sensor unit is directly mated with the connection structure that is integrally formed on a side surface of the monitor main unit.

2. The condition monitoring device according to claim 1, wherein:
    the second sensor unit includes a third connector mateable with the second connector of the first sensor unit and a fourth connector detachably attachable to a third sensor unit carriable by the user;
    data associated with a monitored condition is detected by the third sensor unit is provided to the monitor main unit via the third connector, the second sensor unit, the first sensor unit, and the connection structure and processed by the monitor main unit; and
    the third connector is mateable with the connection structure arranged in the monitor main unit, and the fourth connector is mateable with the first connector arranged in the first sensor unit.

3. The condition monitoring device according to claim 1, wherein:
    the connection structure is a first connection structure arranged in the monitor main unit;
    the monitor main unit further includes a second connection structure differing from the first connection structure;
    the second connection structure enables detachable attachment to a fourth sensor unit carriable by the user;
    data associated with a monitored condition detected by the fourth sensor unit is provided to the monitor main unit via the second connection structure and processed by the monitor main unit;
    the fourth sensor unit includes a fifth connector mateable with the second connection structure and a sixth connector detachably attachable to a fifth sensor unit carriable by the user; and
    data associated with a monitored condition detected by the fifth sensor unit is provided to the monitor main unit via the sixth connector and the fourth sensor unit and processed by the monitor main unit.

4. The condition monitoring device according to claim 3, wherein:
    the fifth sensor unit includes a seventh connector mateable with the sixth connector of the fourth sensor unit and an eighth connector detachably attachable to a sixth sensor unit carriable by the user;
    data associated with a monitored condition detected by the sixth sensor unit is provided to the monitor main unit via the eighth connector and the fourth sensor unit and processed by the monitor main unit; and
    the seventh connection is mateable with the second connection structure of the monitor main unit; and the eighth connector is mateable with the fifth connector of the fourth sensor unit.

5. The condition monitoring device according to claim 3, wherein:
the first connection structure and the second connection structure of the monitor main unit have the same structure;
the first connection structure is mateable with the fifth connector of the fourth sensor unit in addition to the first connector of the first sensor unit; and
the second connection structure is mateable with the first connector of the first sensor unit in addition to the fifth connector of the fourth sensor unit.

6. The condition monitoring device according to claim 1, wherein:
the first sensor unit is one of a plurality of sensor units having connection compatibility and selectable by the user in accordance with varying needs of the user;
the first sensor unit, when electrically connected to the monitor main unit by the user, is communicable with the monitor main unit;
the second sensor unit is one of the plurality of sensor units having connection compatibility and selectable by the user in according with varying needs of the user; and
the second sensor unit, electrically connected to the first sensor unit by the user, is communicable with the monitor main unit via the first sensor unit.

7. The condition monitoring device according to claim 1, wherein the monitor main unit, the first sensor unit, and the second sensor unit are connectable in series.

8. The condition monitoring device according to claim 1, wherein the first sensor unit and the second sensor unit are attachable to and detachable from the supporting member by the user.

9. The condition monitoring device according to claim 1, wherein each of the first sensor unit and the second sensor unit is an external sensor unit and the monitor main unit does not have any built-in sensors for detecting a condition related to the user.

* * * * *